United States Patent [19]

Lotz

[11] Patent Number: 5,270,083

[45] Date of Patent: Dec. 14, 1993

[54] WOOD PRESERVATION SYSTEMS INCLUDING HALOGENATED TANNIN EXTRACTS

[75] Inventor: W. Robert Lotz, Milwaukee, Wis.

[73] Assignee: Cecco Trading, Inc., Milwaukee, Wis.

[21] Appl. No.: 718,946

[22] Filed: Jun. 21, 1991

[51] Int. Cl.⁵ .............................................. A01N 3/00
[52] U.S. Cl. .................................... 428/22; 428/541;
428/907; 106/18.31; 106/18.35; 427/393;
427/297; 427/440
[58] Field of Search .......................... 428/22, 541, 907;
427/440, 297, 393; 560/68, 69; 106/18.31, 18.35

[56] References Cited

U.S. PATENT DOCUMENTS

| | | | |
|---|---|---|---|
| 1,013,913 | 1/1912 | Wemer | 560/68 |
| 1,183,055 | 5/1916 | Wemer | 560/68 |
| 4,661,382 | 4/1987 | Lotz | 106/18.35 |
| 4,732,817 | 3/1988 | Lotz et al. | 428/907 |

OTHER PUBLICATIONS

"The World Book Dictionary" by C. L. Barnhart, vol. Two, L-Z p. 2126.

"Tanning Materials" by A. Harvey, p. 3.
"Vegetable tanning Materials" by F. N. Howes (1953), p. 1.
Webster's Ninth New Collegiate Dictionary, 1990, p. 1205.

*Primary Examiner*—Ellis P. Robinson
*Assistant Examiner*—Nasser Ahmad
*Attorney, Agent, or Firm*—Foley & Lardner

[57] ABSTRACT

The invention relates to wood preservation systems which employ impregnating agents comprising halogenated tannin extracts from plant species which are relatively more resistant to fungi, weathering, rotting, insect attack, etc. Materials contained within the tannin extracts are converted to halogenated substances which are absorbed by the wood species to be treated. The halogenated extract materials can be used with or without other treatment agents (e.g., fixatives or metal salts). Bromine is the preferred halogen material, with optimum treatment occurring when the bromine concentration in the extract exceeds about 2% (most preferably, about 4-5%).

14 Claims, No Drawings

WOOD PRESERVATION SYSTEMS INCLUDING HALOGENATED TANNIN EXTRACTS

BACKGROUND OF THE INVENTION

1. Field of the Invention

The present invention relates generally to the art of wood preservation, and more particularly to the art of increasing the resistance of pressure permeable wood species to the deterioration caused by weathering, leaching or attack by fungi, insects, marine borers, etc. In the principal embodiments of the present invention, such wood preservation is accomplished by using as an impregnating agent a vegetable extract containing tannin which has been halogenated. Still more specifically, in the preferred embodiment the halogenation is accomplished with bromine.

2. Description of the Prior Art

It has been known for many years that certain woods of various types can be preserved by chemical treatment. Creosote, pentachlorophenol, and certain mixtures of copper, chromium and arsenic referred to as "CCA" are several of the better known examples. All of such treatment systems involve one or more drawbacks, principally because they are highly toxic or because they leach from the wood material, thereby leaving the wood unprotected. Other systems are known for coloring wood and many prior art patents describing early attempts at wood preservation are disclosed in U.S. Pat. No. 4,732,817 issued Mar. 22, 1988 to W. Robert Lotz and Donald F. Hollaway for "Wood Preservation".

The aforementioned Lotz, et al. patent not only describes the problems with the prior art but suggests a solution for the problem in which a tannin extract is taken from a plant species which has relatively superior weathering and other resistance properties. Wood to be treated is impregnated with the extract, which is then further processed with an aqueous solution of a fixative to prevent leaching of the extract during use of the wood. The process described in the Lotz, et al. patent can be used not only for wood preservation, but for coloring of the wood and, in that connection, certain metallic salts could also be used. Methods for treating wood in an environmentally suitable manner would represent substantial advances in the art. Products prepared therefrom could be used for aesthetic enhancement or for structural purposes. One feature which has been of some concern with regard to the Lotz, et al. system is the requirement of the use of a fixative, the elimination of which, at least for some applications, would represent a further advance in this technology.

SUMMARY OF THE INVENTION

The present invention provides a unique extract material for converting pressure permeable wood species which are relatively less resistant to weathering and attack by molds, fungi, insects, etc. to wood products which are relatively more resistant thereto and which can provide such properties without the need for a fixative material. The present invention also provides a wood preservation method which is environmentally safe and which can produce treated pressure permeable wood products which will be able to meet or exceed recognized industry standards such as those set by the American Wood Preservers' Association (M10-77) and/or testing under ASTM D-1413.

The present invention also provides wood preservation systems which can be used with the coloring techniques disclosed in the aforementioned Lotz, et al. patent to produce wood products which maintain enhanced properties during extended use and weathering. In a further feature of the invention, the preservation technique is accomplished without the use of expensive, flammable or toxic solvents which would need to be reclaimed in the manufacturing process of many prior systems. Furthermore, the present invention allows conversion of relatively susceptible pressure permeable wood species to treated wood products having vastly improved weathering and decay resistance properties at reasonable cost.

How these and other features of the invention are accomplished will be described in the following detailed description of the preferred and alternate embodiments of the invention. Generally, however, the features are accomplished by first obtaining a tannin extract from a plant species which is known to have desirable weathering and other resistance properties. The extract may be obtained from any part of the plant, such as a tree, leaves, bark, pods, roots, nuts, etc. Several preferred plant species are acacia negra, quebracho, eucalyptus, or any other species identified later herein, the requirement for the extract being that it contains those components of the resistant species which impart the resistant qualities thereto. Such components will usually contain tannins, but they will also contain other substances. The tannin extract is then halogenated, preferably with bromine, in a process which will be described and is then used to impregnate wood. High retention rates are achieved and the wood resulting therefrom has improved properties with regard to fungi resistance, a key measure of its ability to withstand extended periods of use in external environments. Various combinations of the use of the halogenated tannin extract with other treatment techniques will be described in the following detailed description. Other ways in which the foregoing features of the invention are accomplished will become apparent to those skilled in the art after the balance of this specification has been read and understood.

DETAILED DESCRIPTION OF THE PREFERRED AND ALTERNATE EMBODIMENTS

Before proceeding to the description of certain examples which illustrate the process of and the beneficial results obtained by following the teachings of the present invention, it will be helpful to establish several general categories of substances and materials which are useful herein.

First, the wood to be treated can be selected from a wide variety of woods. However, most desirably, such wood will be selected from pressure permeable wood species which are relatively inexpensive, in abundant supply, and yet which do not have particularly good color, weatherability or resistance to molds, fungi, insect infestation, etc. Examples of woods which fall into this category are the firs and pines. These materials will be used in the examples, but it should be understood that other pressure permeable wood species can be treated using the process of the present invention. The woods will hereafter be referred to as the wood receiver.

Second, the tannin extract material to be used in the wood preservation process of the present invention can also be selected from numerous materials, and the particular substances mentioned in this paragraph should be taken as illustrative rather than limiting. In general, the materials comprise spray dried, solid or concentrated solutions of tannin extracts from certain plants, e.g., trees, brush, shrubs. In addition, the extracts can be obtained from a particular part of the plant or a combination of parts, e.g., the root, bark, heartwood, limbs, leaves, pods, nuts, etc. The general requirement for the plant material, which will hereinafter be referred to as the tannin extract donor, is that it have good weatherability, resistance to mold, fungi, attack by various organisms, or have good coloring characteristics, or combinations of the foregoing properties which are superior to that or those of the wood receiver. Examples of plants which may be used as tannin extract donors are as follows (with the principal country or region of availability being shown in parenthesis): wattle, also known as acacia or mimosa (South Africa, South America, especially Brazil); quebracho (Argentina, Paraguay and Brazil); chestnut (France and Italy); myrabolans (India); mangrove (swampy, tropical areas such as southern Florida, Columbia, Brazil, Africa); divi divi (western coast of South America); tara (Peru); sumac (Sicily, Albania and Yugoslavia); cypress (United States); gambier (Malaysia, Sumatra, Borneo); and chestnut oak (blighted in the United States, but available from numerous other sources).

The tannin extracts are obtained in ways similar to those employed in obtaining tannin extracts for use in tanning leather. The tannin extracts useful in the present invention are generally water-soluble and may be obtained by extracting the tannin extract donor in water. The tannin extract donor will typically be used in a comminuted form, so more surface area will be exposed to the extracting liquid. It is desirable for purposes of the present invention to extract as much of the active substances from the tannin extract donor as possible during the extraction step.

Preferably, the solution of tannin extract is then reduced to a powder form, e.g., by evaporation of the water therefrom and spray-drying. Of course, this eliminates the need to transport large amounts of water over long distances, especially in those cases where the source of the tannin extract donor is many, many miles from the location at which the wood receiver will be treated. It has been found that tannin powders, concentrated liquids, or solid tannin extracts have good shelf-life properties and they may be exposed to a wide range of temperatures during transportation.

The tannin extracts, when they are being prepared for use in the system of the present invention, are halogenated after extraction or, if a dried tannin containing material is present, are halogenated after the dried material is dissolved in water. The halogenated tannin extracts can then be used in water solution in widely varying amounts, from 1% or less up to substantially greater concentrations. The preferred range is from about 1 to about weight 20 weight % of the halogenated tannin extract in water.

The extracted tannins heretofore described may, after halogenation, be used as the sole wood preservation material or they may be combined with certain metal salts, such as the metal salts described in the patents referred to in the Lotz, et al. patent. Such salts may be used for a variety of purposes (such as those described in such patents), but I have recognized that they may enhance the preservation properties of the system of the present invention, perhaps synergistically so, and can also be used for coloration effects as well. The amount of metallic salt can also vary widely, but the preferred range is from about 1 to about 10 weight % of the salt in aqueous solution. Examples of metallic salts which are useful herein include zinc salts, chromium salts, copper salts, iron salts, aluminum salts, especially the chlorides and sulfates thereof.

Fixatives may also be used with the halogenated tannin extract solutions of the present invention, and the types of fixative which are preferable are those described in the aforementioned Lotz, et al. patent, i.e., non-ionic surface active agents, especially those which are entirely water soluble in the range of 70° F. to 160° F. and which have an HLB number generally between 7 and 15. As indicated in the Lotz, et al. patent, cationic surface active agents can also be used, but are not preferred.

Examples of suitable non-ionic surfactants which can be used, alone or in combination, in the present invention include sulfonates, laureates, oleates, glycerol compounds, ethoxylate blends, ethoxylated caster oils, ethoxylated fatty acids, oxyethylated alcohols, nonyl phenol ethoxylates and octylphenol ethoxylates, mono and tri-stearates, alkylaryl polyether alcohols and the like. Examples of suitable cationic surfactants which may be used in the practice of the present invention include certain ethoxylated fatty amines, quaternary ammonium chlorides, etc. Numerous directories are commonly available listing surfactants, their type (non-ionic, cationic, etc.) as well as the HLB number and such directories provide guidance in the selection of suitable materials for use in the practice of the present invention.

The fixative may also be used in varying quantities which will depend in large measure on the tannin extract or extract/salt combination employed. The preferred range, however, is 0.1% to 5% parts by weight of the surfactant in water. The amount will also depend in part on the activity level of the surfactant, which as is known to the art, can vary from material to material.

The tannin extracts mentioned previously contain complex phenolic materials which are subject to halogenation at various sites on the aromatic rings. While any of the halogen materials can be used, bromine is preferred for several reasons.

First, the reaction of fluorine or chlorine with phenolic type materials is difficult to control and iodine, while it can be reacted, is more difficult to attach to the phenolic structure. Bromine is a good candidate as the halogenation agent because its use is generally regarded as safe for a variety of other applications from an environmental standpoint, and brominated compounds are frequently used in water treatment chemicals and other materials which have been approved by the relevant regulatory agencies.

By way of example only, wattle extract (acacia negra) will be used as an example of the starting material for the preparation of the treatment solution according to the present invention. An aqueous solution of wattle extract containing about 37–38% solids was prepared and adjusted to a pH of about 8.1 using sodium hydroxide. The pH is maintained above neutral because it has been found that brominated tannin materials are water insoluble below pH 7.2.

The manufacturing technique involves bubbling bromine gas into the extract solution, which is stirred and maintained at room temperature to cause the reaction. To prevent unreacted bromine from escaping the reaction vessel, a spray mist of the extract liquid is directed across the top of the vessel to react with any small amount of bromine that might come through the solution unreacted. This suppression technique not only saves bromine gas (with the resultant cost savings), but prevents undesirable emissions and the unpleasant smell which can result from the use of bromine.

The bromination is continued at a pH above 7.2 to result in a halogenated tannin which is water soluble. The brominated material may then be diluted further for impregnation treatment. It is desirable that the amount of bromine, by weight, be maintained above about 2% (and up to 5% or more) in the solids portion of the extract material. The extract material itself is impregnated into the wood receiver in an autoclave system, as is well known, and the percentage impregnated may vary from about 4% of the weight of the wood, although adequate wood preservation is noted using even less than 1%.

Tests using the brominated wattle extracts have been conducted, using two fungi, *Gloeophyllum trabeum* and *Postia placenta*. Both are brown-rot fungi and are recommended by the standard testing techniques (ASTM D1413 and AWPA M10-77). *Postia placenta* is a copper-tolerant fungus. In the charts that follow, the retentions, weight loss and standard deviations are given.

It will be noted that the fungal strains used were vigorous, as indicated by the high percent weight loss, 59.4% and 62.3%, respectively, obtained for untreated controls. The halogenated extracts have been designated WP-1 (containing approximately 5% total bromine content) and WP-2 (containing approximately 2% total bromine). It will be noted that the higher the bromine content, the better efficacy in protecting the wood from fungal attack.

Further, the charts below indicate that testing was done to see if the halogenated extract material complemented the activity of copper in control of copper-tolerant fungi (in a two step treating process). All of the copper-containing formulations gave complete, or almost complete, control of *G. trabeum*, a non-copper tolerant material. Against the copper-tolerant *P. placenta*, complementation was observed, even in solutions containing as little as 0.5% WP-1. The copper-containing WP-1 formulations controlled this particular fungi better than the equivalent WP-2 formulations without copper. The use of copper is shown and demonstrated in the present invention, even though it is most desirable to use systems which avoid any metallic substances for environmental reasons.

TABLE 1

Retentions and weight losses with standard deviations of soil blocks exposed to monocultures of *Gloeophyllum trabeum* and *Postia placenta* using AWPA Standard M10-77, Standard Method of Testing Wood Preservatives by Laboratory Soil-Block Culture (same as ASTM D-1413).

| TREATING SOLUTION | RETENTION (Kg/m$^3$) | | WT. LOSS | STD. DEV. |
|---|---|---|---|---|
| | 1ST | 2ND | | |
| (% = total solids of extract to wood weight) | | | | |
| I. *Gloeophyllum trabeum* | | | | |
| A. Halogenated extracts - Comparison of Two batches (I & II) | | | | |
| 1. 4% WP-1 | 24.4 | | 0.4% | 0.2% |
| 2. 4% WP-1 (II) | 23.2 | | 0.6% | 0.8% |
| 3. 2% WP-1 | 11.3 | | 1.2% | 1.3% |
| 4. 2% WP-1 (II) (anomaly) | 11.6 | | 21.1% | 7.0% |
| 5. 1% WP-1 | 5.2 | | 7.7% | 2.7% |
| 6. 1% WP-1 (II) (anomaly) | 5.6 | | 21.1% | 7.0% |
| 7. 0.5% WP-1 | 2.3 | | 42.8% | 8.4% |
| 8. 0.5% WP-1 (II) | 3.0 | | 47.1% | 4.9% |
| 9. 0.25% WP-1 | 1.5 | | 55.2% | 5.8% |
| 10. 0.25% WP-1 (II) | 1.5 | | 58.6% | 5.6% |
| 11. 4% WP-2 | 21.1 | | 22.8% | 19.4% |
| 12. 4% WP-2 (II) | 26.0 | | 22.6% | 7.5% |
| 13. 2% WP-2 | 11.6 | | 41.7% | 3.9% |
| 14. 2% WP-2 (II) | 12.9 | | 50.2% | 7.4% |
| 15. 1% WP-2 | 4.9 | | 51.3% | 3.5% |
| 16. 1% WP-2 (II) | 6.5 | | 62.4% | 1.8% |
| 17. 0.5% WP-2 | 2.4 | | 50.6% | 9.2% |
| 18. 0.5% WP-2 (II) | 3.3 | | 62.6% | 2.9% |
| 19. 0.25% WP-2 | 1.3 | | 57.5% | 8.5% |
| 20. 0.25% WP-2 (II) | 1.6 | | 65.5% | 1.5% |
| B. Halogenated extracts + co-biocide | | | | |
| 21. 4% WP-1 + 4% CuSO$_4$ | 22.8 | 27.3 | 0.8% | 0.2% |
| 22. 2% WP-1 + 2% CuSO$_4$ | 11.9 | 13.5 | 1.1% | 0.3% |
| 23. 1% WP-1 + 1% CuSO$_4$ | 5.1 | 6.6 | 0.6% | 0.5% |
| 24. 0.5% WP-1 + 0.5% CuSO$_4$ | 2.4 | 3.2 | 0.8% | 0.5% |
| 25. 0.25% WP-1 + 0.25% CuSO$_4$ | 1.2 | 1.8 | 2.0% | 0.8% |
| 26. 4% WP-2 + 4% CuSO$_4$ | 21.6 | 26.5 | 1.1% | 0.3% |
| 27. 2% WP-2 + 2% CuSO$_4$ | 11.2 | 12.9 | 1.3% | 0.4% |
| 28. 1% WP-2 + 1% CuSO$_4$ | 5.0 | 6.5 | 1.0% | 0.1% |
| 29. 0.5% WP-2 + 0.5% CuSO$_4$ | 2.4 | 3.1 | 1.8% | 0.4% |
| 30. 0.25% WP-2 + 0.25% CuSO$_4$ | 1.3 | 1.7 | 5.3% | 5.3% |
| C. Controls | | | | |
| 39. 4% CuSO$_4$ | 26.2 | | 0.4% | 0.3% |
| 40. 2% CuSO$_4$ | 12.5 | | 0.4% | 0.2% |
| 41. 1% CuSO$_4$ | 6.0 | | 0.5% | 0.5% |
| 42. 0.5% CuSO$_4$ | 3.1 | | 1.9% | 0.4% |
| 43. 0.25% CuSO$_4$ | 1.5 | | 4.2% | 1.1% |
| 44. 1% CCA | 6.3 | | 0.8% | 0.2% |
| 45. 0.5% CCA | 3.3 | | 0.7% | 0.2% |
| 46. 0.25% CCA | 1.5 | | 1.6% | 0.2% |

TABLE 1-continued

Retentions and weight losses with standard deviations of soil blocks exposed to monocultures of *Gloeophyllum trabeum* and *Postia placenta* using AWPA Standard M10-77, Standard Method of Testing Wood Preservatives by Laboratory Soil-Block Culture (same as ASTM D-1413).

| TREATING SOLUTION | RETENTION (Kg/m$^3$) 1ST | 2ND | WT. LOSS | STD. DEV. |
|---|---|---|---|---|
| 47. Untreated | | | 59.4% | 7.4% |
| II. *Postia placenta* | | | | |
| A. Halogenated extracts - Comparison of Two batches (I & II) | | | | |
| 1. 4% WP-1 | 25.5 | | 0.3% | 0.1% |
| 2. 4% WP-1 (II) | 26.5 | | 0.5% | 0.2% |
| 3. 2% WP-1 | 12.3 | | 0.6% | 0.3% |
| 4. 2% WP-1 (II) | 12.6 | | 0.3% | 0.1% |
| 5. 1% WP-1 | 5.5 | | 10.7% | 20.4% |
| 6. 1% WP-1 (II) (anomaly) | 6.3 | | 28.5% | 21.3% |
| 7. 0.5% WP-1 | 2.6 | | 43.1% | 24.2% |
| 8. 0.5% WP-1 (II) | 3.0 | | 57.3% | 2.2% |
| 9. 0.25% WP-1 | 1.1 | | 57.4% | 2.8% |
| 10. 0.25% WP-1 (II) | 1.5 | | 59.0% | 4.4% |
| 11. 4% WP-2 | 24.4 | | 40.7% | 4.7% |
| 12. 4% WP-2 (II) | 25.4 | | 27.3% | 23.8% |
| 13. 2% WP-2 | 11.9 | | 58.6% | 1.8% |
| 14. 2% WP-2 (II) | 12.8 | | 55.6% | 7.2% |
| 15. 1% WP-2 | 5.0 | | 59.3% | 2.9% |
| 16. 1% WP-2 (II) | 6.4 | | 57.3% | 4.9% |
| 17. 0.5% WP-2 | 2.3 | | 59.3% | 2.9% |
| 18. 0.5% WP-2 (II) | 3.2 | | 56.9% | 2.7% |
| 19. 0.25% WP-2 | 1.2 | | 62.2% | 2.8% |
| 20. 0.25% WP-2 (II) | 1.6 | | 58.6% | 3.8% |
| B. Halogenated extracts + co-biocide | | | | |
| 21. 4% WP-1 + 4% CuSO$_4$ | 24.9 | 27.5 | 1.4% | 0.1% |
| 22. 2% WP-1 + 2% CuSO$_4$ | 12.2 | 13.7 | 1.4% | 0.3% |
| 23. 1% WP-1 + 1% CuSO$_4$ | 5.6 | 6.9 | 2.1% | 0.9% |
| 24. 0.5% WP-1 + 0.5% CuSO$_4$ | 2.4 | 3.2 | 7.9% | 8.9% |
| 25. 0.25% WP-1 + 0.25% CuSO$_4$ | 1.2 | 1.8 | 50.7% | 2.5% |
| 26. 4% WP-2 + 4% CuSO$_4$ | 24.1 | 27.1 | 2.7% | 1.0% |
| 27. 2% WP-2 + 2% CuSO$_4$ | 11.3 | 13.1 | 19.4% | 9.9% |
| 28. 1% WP-2 + 1% CuSO$_4$ | 4.8 | 6.8 | 38.6% | 5.5% |
| 29. 0.5% WP-2 + 0.5% CuSO$_4$ | 2.3 | 3.3 | 49.6% | 3.6% |
| 30. 0.25% WP-2 + 0.25% CuSO$_4$ | 1.2 | 1.8 | 54.1% | 3.7% |
| C. Controls | | | | |
| 39. 4% CuSO$_4$ | 26.1 | | 45.9% | 5.3% |
| 40. 2% CuSO$_4$ | 13.4 | | 51.9% | 3.7% |
| 41. 1% CuSO$_4$ | 6.4 | | 46.2% | 5.0% |
| 42. 0.5% CuSO$_4$ | 3.2 | | 48.0% | 6.8% |
| 43. 0.25% CuSO$_4$ | 1.6 | | 54.2% | 6.5% |
| 44. 1% CCA | 6.2 | | 0.4% | 0.1% |
| 45. 0.5% CCA | 3.2 | | 0.6% | 0.2% |
| 46. 0.25% CCA | 1.6 | | 2.6% | 1.3% |
| 47. Untreated | | | 62.3% | 7.1% |

While the present invention has been described in connection with fungal control using two specific materials, the invention has much wider applicability. Similar protection will be achieved with other fungi and the wood treatments can be used to impart improved weathering properties, prevention of insect attack, and the other characteristics previously noted for the Lotz, et al. systems. It will further be noted from the charts that fixatives have not been used, but they certainly can be, with or without the metallic salts, in connection with the systems described in my earlier patent referred to above.

While in the present invention, certain preferred materials and processing sequences have been described, the invention can be variously adapted by one skilled in the art after the present specification has been read and understood. Hence, the foregoing description of the invention is not to be taken as limiting as to its scope, but rather the scope of the present invention is to be limited solely by the scope of the claims which follow.

What is claimed is:

1. An organic, solvent-free wood preserving process for treating a pressure permeable wood species having relatively poor resistance to fungal attack, decay or weathering, leaching, insect attack, which comprises the steps of:
   a) preparing an aqueous solution at a pH of 7.2 or greater of a vegetable tannin extract obtained from one or more components from one or more plant materials which are relatively more resistant to fungal attack, decay, weathering, leaching, or insect attack;
   b) halogenating the extract contained within said aqueous solution to a halogen content of about 2% to about 5% by weight of the dry weight of the extract;
   c) impregnating said wood species with said halogenated extract.

2. The process set forth in claim 1, wherein said step of halogenating the tannin extract comprises bromination of said extract.

3. The process set forth in claim 1, wherein said plant material is selected from the group consisting of acacia negra, quebracho, chestnut, myrabolans, mangrove, tara, eucalyptus, divi divi, sumac, cypress, gambier, or chestnut oak.

4. The process of claim 1, comprising the further step of subsequently impregnating said wood species with a fixative selected from the group consisting of aqueous solutions of non-ionic surface active agents or cationic surface active agents, wherein said surface active agent comprises from about 0.1 to about 5 wt. % of said aqueous solution.

5. The process set forth in claim 4, wherein said fixative is an aqueous solution of one or more non-ionic surface active agents having HLB numbers in the range of about 7 to about 15.

6. The process of claim 1, wherein said process includes the further step of impregnating said wood species with an aqueous solution of metallic salt.

7. The process set forth in claim 6, wherein the metal salt is selected from the group consisting of zinc, aluminum, chromium, iron and copper salts.

8. The process of claim 1, wherein the halogenated extract is impregnated into said wood species using an aqueous solution containing about 1 to about 20 weight % of the extract.

9. A treated wood product prepared by an organic, solvent-free wood preserving process comprising the step of impregnating a pressure permeable wood species having relatively poorer resistance to decay, weathering, leaching, insect attack, fungal attack or the like, with an aqueous solution of a halogenated vegetable tannin extract having a halogen content of about 2% to about 5% by weight of the dry weight of the extract and a pH of 7.2 or greater, wherein said tannin extract is obtained from one or more components of a plant species which has a relatively greater resistance to decay, weathering, leaching, insect attack or fungal attack.

10. The wood product of claim 9, wherein said halogenated tannin extract is a brominated tannin extract.

11. The wood product of claim 10, wherein the wood is impregnated with a halogenated tannin extract in an amount of from about 1% to about 7% by weight based on the weight of said wood.

12. The wood product of claim 9, wherein the wood to be impregnated is selected from the group consisting of pines and firs.

13. The wood product of claim 9, wherein said plant species is selected from the group consisting of acacia negra, quebracho, chestnut, myrabolans, mangrove, tara, eucalyptus, divi divi, sumac, cypress, gambier, or chestnut oak.

14. The wood product of claim 9, wherein said wood product further is impregnated with one or more aqueous solutions wherein the solutes are selected from the group consisting of metallic salts, non-ionic surface active agents, or cationic surface active agents.

* * * * *